US009527007B2

(12) United States Patent
Whitchurch (10) Patent No.: US 9,527,007 B2
(45) Date of Patent: *Dec. 27, 2016

(54) PROCESSES AND APPARATUSES FOR SEPARATING STREAMS TO PROVIDE A TRANSALKYLATION FEED STREAM IN AN AROMATICS COMPLEX

(71) Applicant: UOP LLC, Des Plaines, IL (US)

(72) Inventor: Patrick C. Whitchurch, Sleepy Hollow, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/726,151

(22) Filed: May 29, 2015

(65) Prior Publication Data

US 2016/0346711 A1    Dec. 1, 2016

(51) Int. Cl.
| | | |
|---|---|---|
| B01D 3/00 | (2006.01) | |
| B01D 3/14 | (2006.01) | |
| C07C 5/00 | (2006.01) | |
| C07C 5/22 | (2006.01) | |
| C07C 5/27 | (2006.01) | |
| C07C 6/00 | (2006.01) | |
| C07C 6/02 | (2006.01) | |
| C07C 6/04 | (2006.01) | |
| C07C 7/00 | (2006.01) | |
| C07C 7/04 | (2006.01) | |
| B01J 19/00 | (2006.01) | |

(Continued)

(52) U.S. Cl.
CPC ............... *B01D 3/141* (2013.01); *B01J 19/24* (2013.01); *C07C 5/2732* (2013.01); *C07C 6/06* (2013.01); *C07C 7/04* (2013.01); *C10G 35/04* (2013.01); *B01J 2219/24* (2013.01)

(58) Field of Classification Search
CPC ............. B01D 3/00; B01D 3/14; B01D 3/141; C07C 5/00; C07C 5/22; C07C 5/27; C07C 5/2729; C07C 5/2732; C07C 6/00–6/06; C07C 7/00; C07C 7/04; B01J 19/00; B01J 19/24; B01J 2219/24; C10G 35/00; C10G 35/04

See application file for complete search history.

(56) References Cited

U.S. PATENT DOCUMENTS 6,376,733 B1 *  4/2002  Ferraro .................. C07C 7/005
                                                              585/321
6,740,788 B1     5/2004  Maher
(Continued)

OTHER PUBLICATIONS

Slade, "Dividing Wall Column Revamp Optmises Mixed Xylenes Production", Topical Conference on Distillation, Symposium Series No. 152, 2006 IChemE, 10 pages.

(Continued)

*Primary Examiner* — Natasha Young (57) ABSTRACT

A process and apparatus for the production of at least one xylene isomer is provided. The process includes passing a first stream to one side of a split shell fractionation column and a second stream to the other side of the column. The second stream has a higher ratio of ethylbenzene to total $C_8$ aromatics than the first stream. A first overhead stream from the one side is separated and passed as a mixed xylene product and a second overhead stream from the other side is separated and passed as feed to a para-xylene separation zone.

6 Claims, 4 Drawing Sheets

(51) Int. Cl.
*B01J 19/24* (2006.01)
*C10G 35/00* (2006.01)
*C10G 35/04* (2006.01)
*C07C 6/06* (2006.01)

(56) References Cited

U.S. PATENT DOCUMENTS

| | | | |
|---|---|---|---|
| 7,371,912 B2 * | 5/2008 | Schultz | C07C 5/2702 |
| | | | 585/477 |
| 7,556,717 B2 * | 7/2009 | Heida | B01D 3/141 |
| | | | 203/27 |
| 8,716,545 B1 * | 5/2014 | Corradi | C07C 7/04 |
| | | | 585/802 |
| 8,822,747 B2 | 9/2014 | Corradi | |
| 8,877,014 B2 | 11/2014 | Corradi | |
| 2012/0048720 A1 | 3/2012 | Werba | |
| 2014/0155667 A1 * | 6/2014 | Ou | C07C 4/18 |
| | | | 585/479 |
| 2015/0037223 A1 | 2/2015 | Corradi | |

OTHER PUBLICATIONS

Parkinson, "Dividing-Wall Columns Find Greater Appeal", Chemical Engineering Progress, vol. 103(5), www.aiche.org/cep, May 2007, 4 pages.
U.S. Appl. No. 14/726,113, filed May 29, 2015, Whitchurch.

* cited by examiner

PROCESSES AND APPARATUSES FOR SEPARATING STREAMS TO PROVIDE A TRANSALKYLATION FEED STREAM IN AN AROMATICS COMPLEX

FIELD

This present disclosure relates to separation of hydrocarbons in an aromatics complex and more specifically, to the separation of aromatics compounds used as feed for transalkylation within an aromatics-processing complex producing xylene isomers.

BACKGROUND

The xylene isomers are produced in large volumes from petroleum as feedstocks for a variety of important industrial chemicals. The most important of the xylene isomers is para-xylene, the principal feedstock for polyester, which continues to enjoy a high growth rate from large base demand. Ortho-xylene is used to produce phthalic anhydride, which supplies high-volume but relatively mature markets. Meta-xylene is used in lesser but growing volumes for such products as plasticizers, azo dyes and wood preservers. Ethylbenzene generally is present in xylene mixtures and is occasionally recovered for styrene production, but is usually considered a less-desirable component of $C_8$ aromatics.

Among the aromatic hydrocarbons, the overall importance of xylenes rivals that of benzene as a feedstock for industrial chemicals. Xylenes and benzene are produced from petroleum by reforming naphtha but not in sufficient volume to meet demand, thus conversion of other hydrocarbons is necessary to increase the yield of xylenes and benzene. Often toluene is de-alkylated to produce benzene or selectively disproportionated to yield benzene and $C_8$ aromatics from which the individual xylene isomers are recovered.

An aromatics complex flow scheme has been disclosed by Meyers in the Handbook of Petroleum Refining Processes, 2d. Edition in 1997 by McGraw-Hill, and is incorporated herein by reference.

Traditional aromatics complexes send toluene to a transalkylation zone to generate desirable xylene isomers via transalkylation of the toluene with $A_9$ components. $A_9$ components are present in both the reformate bottoms and the transalkylation effluent. $A_9$ components may also be present to some extent in an isomerization effluent. No effort is currently made to separate the $A_9$ components based on their source or particular structure.

SUMMARY

According to an aspect, a process for producing one or more xylenes includes passing a first stream comprising xylenes and $C_9$+ aromatic at a first ratio of ethylbenzene to total $C_8$ aromatics to one side of a split shell fractionation column including a vertical baffle separating the one side from another side. The process further includes passing a second stream comprising xylenes and $C_9$+ aromatic compounds at a second higher ratio of ethylbenzene to total $C_8$ aromatics than the first ratio to the other side of the split shell fractionation column. The process includes a first overhead stream from one side that is separated and passed as a mixed xylene product and a second overhead stream from the other side is separated and passed as feed to a para-xylene separation zone. A mixed xylene product is taken from the side containing a higher ratio of ethylbenzene to total $C_8$ aromatics. A common bottoms stream is sent to a transalkylation zone.

According to an aspect, a process for producing one or more xylenes includes passing a first stream comprising at least a portion of a transalkylation zone effluent stream including $C_9$+ aromatic compounds to a first side of a first split shell fractionation column including a vertical baffle separating the first side from a second side. The process also includes passing a second stream comprising at least a portion of a reformate stream including $C_9$+ aromatic compounds to the second side of the first split shell fractionation column. The process includes a first overhead stream from the one side is separated and passed as a mixed xylene product and a second overhead stream from the other side is separated and passed as feed to a para-xylene separation zone. The mixed xylene product may be taken from the side comprising the reformate stream. A common bottoms stream is sent to a second fractionation column. The process further includes further processing the bottom stream from the first fractionation column in the second fractionation column.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

The following description is not to be taken in a limiting sense, but is made merely for the purpose of describing the general principles of exemplary aspects. The scope of the present disclosure should be determined with reference to the claims.

The feedstream to the present process generally comprises alkylaromatic hydrocarbons of the general formula $C_6H_{(6-n)}R_n$, where n is an integer from 0 to 5 and each R may be $CH_3$, $C_2H_5$, $C_3H_7$, or $C_4H_9$, in any combination. The aromatics-rich feed stream to the process of the present disclosure may be derived from a variety of sources, including without limitation catalytic reforming, steam pyrolysis of naphtha, distillates or other hydrocarbons to yield light olefins and heavier aromatics-rich byproducts (including gasoline-range material often referred to as "pygas"), and catalytic or thermal cracking of distillates and heavy oils to yield products in the gasoline range. Products from pyrolysis or other cracking operations generally will be hydrotreated according to processes well known in the industry before being charged to the complex in order to remove sulfur, olefins and other compounds which would affect product quality and/or damage catalysts or adsorbents employed therein. Light cycle oil from catalytic cracking also may be beneficially hydrotreated and/or hydrocracked according to known technology to yield products in the gasoline range; the hydrotreating preferably also includes catalytic reforming to yield the aromatics-rich feed stream. If the feed stream is catalytic reformate, the reformer preferably is operated at high severity to achieve high aromatics yield with a low concentration of nonaromatics in the product.

Figure 1:
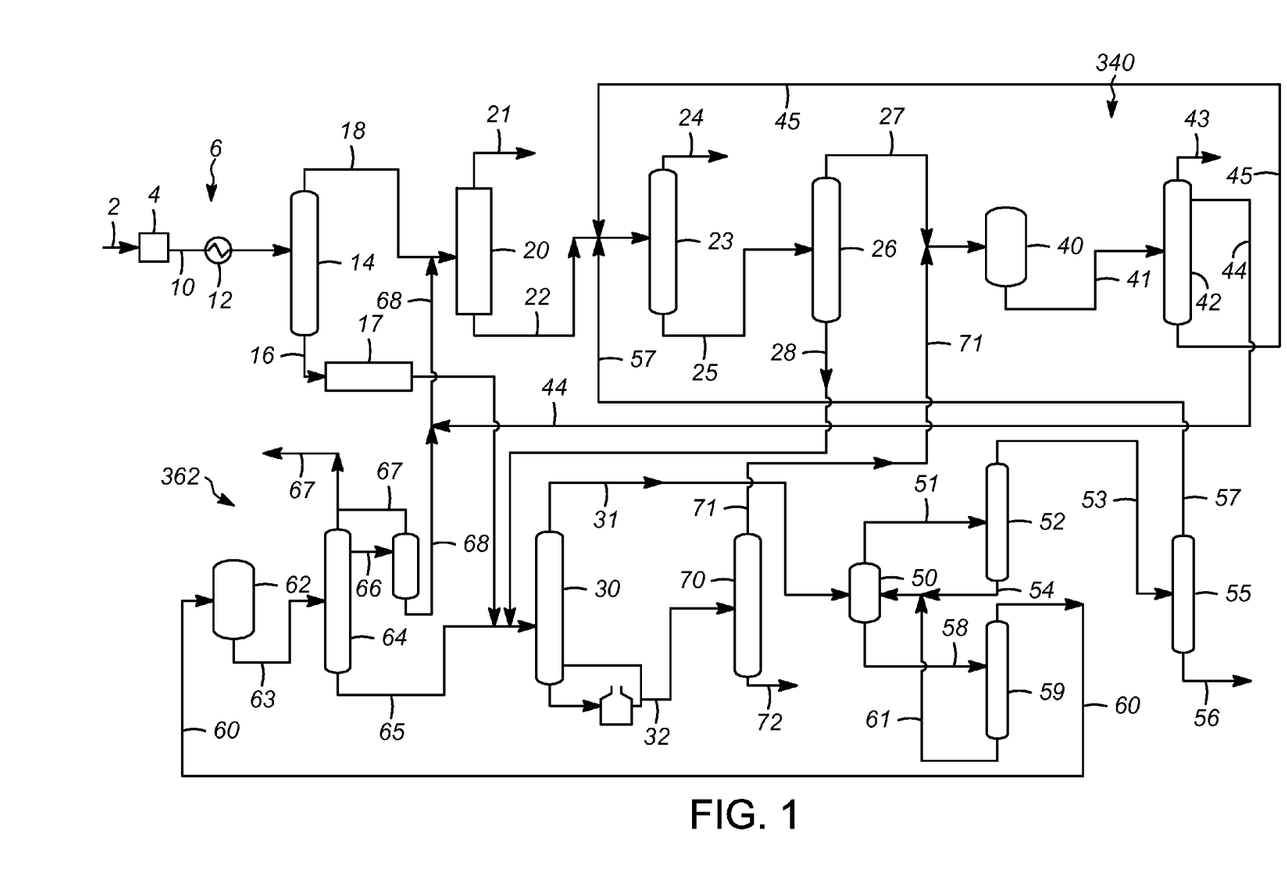
FIG. 1 schematically illustrates an aromatics complex.

FIG. 1 is a simplified flow diagram of an exemplary aromatics-processing complex of the known art directed to the production of at least one xylene isomer. The complex may process an aromatics-rich feed which has been derived, for example, from catalytic reforming in a reforming zone 6. The reforming zone generally includes a reforming unit 4 that receives a feed via conduit 2. The reforming unit will typically comprises a reforming catalyst. Usually such a stream will also be treated to remove olefinic compounds and light ends, e.g., butanes and lighter hydrocarbons and preferably pentanes; such removal, however, is not essential to the practice of the broad aspects of this disclosure and is not shown. The aromatics-containing feed stream contains benzene, toluene and $C_8$ aromatics and typically contains higher aromatics and aliphatic hydrocarbons including naphthenes.

The feed stream is passed via conduit 10 via a heat exchanger 12 to reformate splitter 14 and distilled to separate a stream comprising $C_8$ and heavier aromatics, withdrawn as a bottoms stream via a bottoms outlet 15 in conduit 16, from toluene and lighter hydrocarbons recovered overhead via conduit 18. The toluene and lighter hydrocarbons are sent to extractive distillation process unit 20 which separates a largely aliphatic raffinate in conduit 21 from a benzene-toluene aromatics stream in conduit 22. The aromatics stream in conduit 22 is separated, along with stripped transalkylation product in conduit 45 and overhead from para-xylene finishing column in conduit 57, in benzene column 23 into a benzene stream in conduit 24 and a toluene-and-heavier aromatics stream in conduit 25 which is sent to a toluene column 26. Toluene is recovered overhead from this column in conduit 27 and may be sent partially or totally to a transalkylation unit 40 as shown and discussed hereinafter.

A bottoms stream from the toluene column 26 is passed via conduit 28, along with bottoms from the reformate splitter in conduit 16, after treating via clay treater 17, and recycle $C_8$ aromatics in conduit 65, to fractionator 30. The fractionator 30 separates concentrated $C_8$ aromatics as overhead in conduit 31 from a high-boiling stream comprising $C_9$, $C_{10}$ and heavier aromatics as a bottoms stream in conduit 32. This bottoms stream is passed in conduit 32 to heavies column 70. The heavy-aromatics column provides an overhead stream in conduit 71 containing $C_9$ and at least some of the $C_{10}$ aromatics, with higher boiling compounds, primarily $C_{11}$ and higher alkylaromatics, being withdrawn as a bottoms stream via conduit 72.

The $C_9$+ aromatics from heavies column in conduit 71 is combined with the toluene-containing overhead contained in conduit 27 as feed to transalkylation reactor 40, which contains a transalkylation catalyst as known in the art to produce a transalkylation product comprising benzene through $C_{11}$+ aromatics with xylenes as the focus. The transalkylation product in conduit 41 is stripped in stripper 42 to remove gases in conduit 43 and $C_6$ and lighter hydrocarbons which are returned via conduit 44 to extractive distillation 20 for recovery of light aromatics and purification of benzene. Bottoms from the stripper are sent in conduit 45 to benzene column 23 to recover benzene product and unconverted toluene.

The $C_8$-aromatics overhead provided by fractionator 30 contains para-xylene, meta-xylene, ortho-xylene and ethylbenzene and passes via conduit 31 to para-xylene separation process 50. The separation process operates, preferably via adsorption employing a desorbent, to provide a mixture of para-xylene and desorbent via conduit 51 to extract column 52, which separates para-xylene via conduit 53 from returned desorbent in conduit 54; the para-xylene is purified in finishing column 55, yielding a para-xylene product via conduit 56 and light material which is returned to benzene column 23 via conduit 57. A non-equilibrium mixture of $C_8$-aromatics raffinate and desorbent from separation process 50 is sent via conduit 58 to raffinate column 59, which separates a raffinate for isomerization in conduit 60 from returned desorbent in conduit 61.

The raffinate, comprising a non-equilibrium mixture of xylene isomers and ethylbenzene, is sent via conduit 60 to isomerization reactor 62. The raffinate is isomerized in reactor 62, which contains an isomerization catalyst to provide a product approaching equilibrium concentrations of $C_8$-aromatic isomers. The product is passed via conduit 63 to deheptanizer 64, which removes $C_7$ and lighter hydrocarbons with bottoms passing via conduit 65 to xylene column 30 to separate $C_9$ and heavier materials from the isomerized $C_8$-aromatics. Overhead liquid from dehepta­nizer 64 is sent to stripper 66, which removes light materials overhead in conduit 67 from $C_6$ and $C_7$ materials which are sent via conduit 68 to the extractive distillation unit 20 for recovery of benzene and toluene values.

There are many possible variations of this scheme within the known art, as the skilled routineer will recognize. For example, the entire $C_6$-$C_8$ reformate or only the benzene-containing portion may be subjected to extraction. Para-xylene may be recovered from a $C_8$-aromatic mixture by crystallization rather than adsorption. Meta-xylene as well as para-xylene may be recovered from a $C_8$-aromatic mixture by adsorption, and ortho-xylene may be recovered by fractionation. Alternatively, the $C_9$- and heavier stream or the heavy-aromatics stream is processed using solvent extraction or solvent distillation with a polar solvent or stripping with steam or other media to separate highly condensed aromatics as a residual stream from $C_9$+ recycle to transalkylation. In some cases, the entire heavy-aromatic stream may be processed directly in the transalkylation unit. The present disclosure is useful in these and other variants of an aromatics-processing scheme, aspects of which are described in U.S. Pat. No. 6,740,788 which is incorporated herein by reference.

Figure 2:
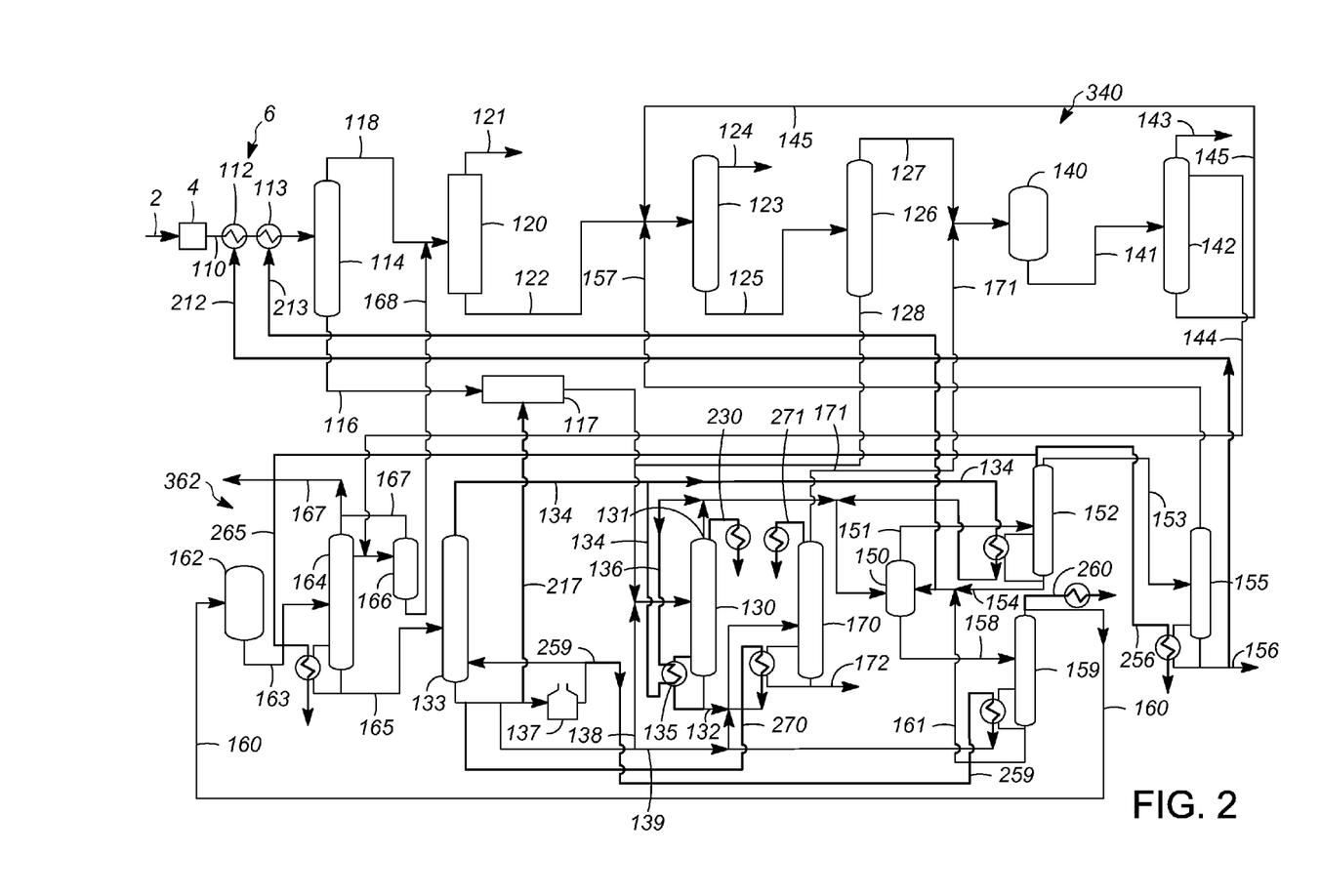
FIG. 2 illustrates an energy-efficient aromatics complex.

Referring to FIG. 2, another exemplary aromatics complex with modifications to improve energy efficiency is illustrated. The energy-efficient aromatics complex is described in U.S. Patent Publication No. 2012/0048720, which is incorporated by reference herein, in its entirety. For ease of reference, a parallel numbering apparatus is employed to those of FIGS. 1 and 2 and similar elements will not be described herein in detail. It should be noted that several variations of the process flow and equipment in this complex are possible, and contemplated herein. The energy efficient aromatics complex includes first and second xylene columns 130 and 133. In this example, first xylene column 130 is a low-pressure column while second xylene column is a high-pressure column. In the reforming zone 106, the feed stream is passed via conduit 102 to reforming unit 104 which includes a reforming catalyst, as is known in the art and described above with regard to FIG. 1. The reformate is passed via conduit 110 via heat exchangers 112 and 113, which raise the temperature of the feed stream, to reformate splitter 114. The heat exchange may supplied via conduits 212 and 213 respectively from the net para-xylene product and the recovered para-xylene separation process recovered desorbent as discussed later in this section.

As in FIG. 1, $C_8$ and heavier aromatics are withdrawn as a bottoms stream via bottoms outlet in conduit 116 while toluene and lighter hydrocarbons recovered overhead via conduit 118 are sent to extractive distillation process unit 120 which separates a largely aliphatic raffinate in conduit 121 from a benzene-toluene aromatics stream in conduit 122. The aromatics stream in conduit 122 is separated, along with stripped transalkylation product in conduit 144 and overhead from para-xylene finishing column in conduit 157, in fractionator 123 into a benzene stream in conduit 124 and a toluene-and-heavier aromatics stream in conduit 125 which is sent to a toluene column 126. Toluene is recovered overhead from this column in conduit 127 and may be sent partially or totally to a transalkylation unit 140 as shown and discussed hereinafter.

A bottoms stream from the toluene column 126 is passed via conduit 128, along with bottoms from the reformate splitter in conduit 116, after treating via clay treater 117, and recycle $C_8$ aromatics in conduit 138, to low-pressure xylene column 130. Other $C_8$-aromatics streams having significant contents of $C_9$ and heavier aromatics, including streams obtained from sources outside the complex, also may be processed in this column; a portion of deheptanizer bottoms in stream 165 also may be included depending on overall energy balances. The low-pressure xylene column separates concentrated $C_8$ aromatics as overhead in conduit 131 from a high-boiling stream comprising $C_9$, $C_{10}$ and heavier aromatics as a bottoms stream in conduit 132.

Simultaneously, an isomerized $C_8$-aromatics stream is passed via conduit 165 to a high-pressure second xylene column 133. This is characterized as a lower-boiling feed stream which contains a lower concentration of heavy materials subject to decomposition than the feed to column 130, and the column pressure thus can be increased in order to effect energy savings. Other $C_8$-aromatics-containing streams having similarly low contents of $C_9$-and-heavier aromatics, including streams obtained from sources outside the complex, also may be contained in the feed stream to this column. The second xylene column separates a second $C_8$-aromatics stream as overhead in conduit 134 from a second $C_9$-and-heavier stream in conduit 139. At least a portion of overhead vapor from the high-pressure xylene column in conduit 134 preferably is employed to reboil low-pressure xylene column 130 in reboiler 135, leaving as a condensed liquid to the xylene-separation process 150 in conduit 136 as well as reflux (not shown) to column 133. In addition, the overhead in conduit 134 preferably is used to provide energy to the reboiler of extract column 152 as well as other such services which are described later or will be apparent to the skilled routineer.

The $C_9$+ bottoms stream passing to reboiler 137 may provide energy via one or both of the stream before the reboiler in conduit 270 and the heated stream from the reboiler in conduit 259 for reboiling respectively one or both of heavy-aromatics column 170 and raffinate column 159; the bottoms stream after heat exchange would be sent to the heavy-aromatics column 170. Other similar heat-exchange services will be apparent to the skilled routineer. The net bottoms stream in conduit 138 usually is passed through column 130 or may be in conduit 139 combined directly with the stream in conduit 132 to heavies column 170. The heavies column provides an overhead a stream in conduit 171 containing $C_9$ and at least some of the $C_{10}$ aromatics, with higher boiling compounds, primarily $C_{11}$ and higher alkylaromatics, being withdrawn as a bottoms stream via conduit 172. This column may be reboiled by xylene column bottoms in conduit 270, as discussed above. Overhead vapor from columns 130 and 170 also may generate steam respectively via conduits 230 and 271 as indicated, with condensed liquids either serving as reflux to each column or as net overhead respectively in streams 131 or 171.

The $C_9$+ aromatics from heavies column in conduit 171 is combined with the toluene-containing overhead contained in conduit 127 as feed to transalkylation reactor 140 to produce a transalkylation product containing xylenes. The transalkylation product in conduit 141 is stripped in stripper 142 to remove gases in conduit 143 and $C_7$ and lighter liquids which are returned via conduit 144 to extractive distillation 120 for recovery of light aromatics following stabilization in isomerate stripper 166. Bottoms from the stripper are sent in conduit 145 to benzene column 123 to recover benzene product and unconverted toluene.

The first and second $C_8$-aromatics streams provided by xylene columns 130 and 133, containing para-xylene, meta-xylene, ortho-xylene and ethylbenzene, pass via conduit 131 and 136 to xylene-isomer separation process 150. The description herein may be applicable to the recovery of one or more xylene isomers other than para-xylene; however, the description is presented for para-xylene for ease of understanding. The separation process operates via a moving-bed adsorption process to provide a first mixture of para-xylene and desorbent via conduit 151 to extract column 152, which separates para-xylene via conduit 153 from returned desorbent in conduit 154. Extract column 152 preferably is operated at an elevated pressure, at least about 300 kPa and more preferably about 500 kPa or higher, such that the overhead from the column is at sufficient temperature to reboil finishing column 155 via conduit 256 or deheptanizer 164 via conduit 265. Heat supplied for reboiling duty via conduits 256 and 265 results in the condensation of the extract in these streams which is either or both refluxed to column 152 (not shown) or sent as a net stream in conduit 153 to finishing column 155. The para-xylene is purified in finishing column 155, yielding a para-xylene product via conduit 156 and light material which is returned to benzene column 123 via conduit 157.

A second mixture of raffinate, as a non-equilibrium blend of $C_8$ aromatics, and desorbent from separation process 150 is sent via conduit 158 to raffinate column 159, which separates a raffinate to isomerization in conduit 160 from returned desorbent in conduit 161. The raffinate column may be operated at higher pressure to generate steam via conduit 260 or to exchange heat in other areas of the complex; condensed liquids from such heat exchange either serve as reflux to the raffinate column or as net overhead in conduit 160. Recovered desorbent in conduits 154 and 161 and net finishing column bottoms may heat the incoming feed stream in conduit 110 via conduits 213 and 212, respectively. In an energy-efficient aromatics complex, the first fractionation column may be operated at a low pressure to separate a first $C_8$-aromatics stream from a first $C_9$-and-heavier aromatics stream, the second fractionation column may be operated at an elevated pressure to separate a second $C_8$-aromatics stream from a second $C_9$-and-heavier aromatics stream. In this regard, an overhead stream from the second column may be circulated to provide heat to a reboiler of the first column. The low pressure typically is between 100 and 800 kPa and the elevated pressure is chosen to enable heat transfer from the first column to the second and typically is at least about 400 kPa above the low pressure.

The stream to the second column may contains less than about 10 weight-% $C_9+$ aromatics, more often less than about 5 weight-% $C_9+$ aromatics, and frequently less than about 2 weight-% $C_9+$ aromatics. The complex may also allow operating the second fractionation column at a pressure that would enable the overhead to provide heat to generate steam useful in an associated processing complex. Further, the $C_8$-aromatics fractionator may comprise three or more columns comprising additional heat exchange between overheads and reboilers in an analogous manner to the above description.

Figure 3:
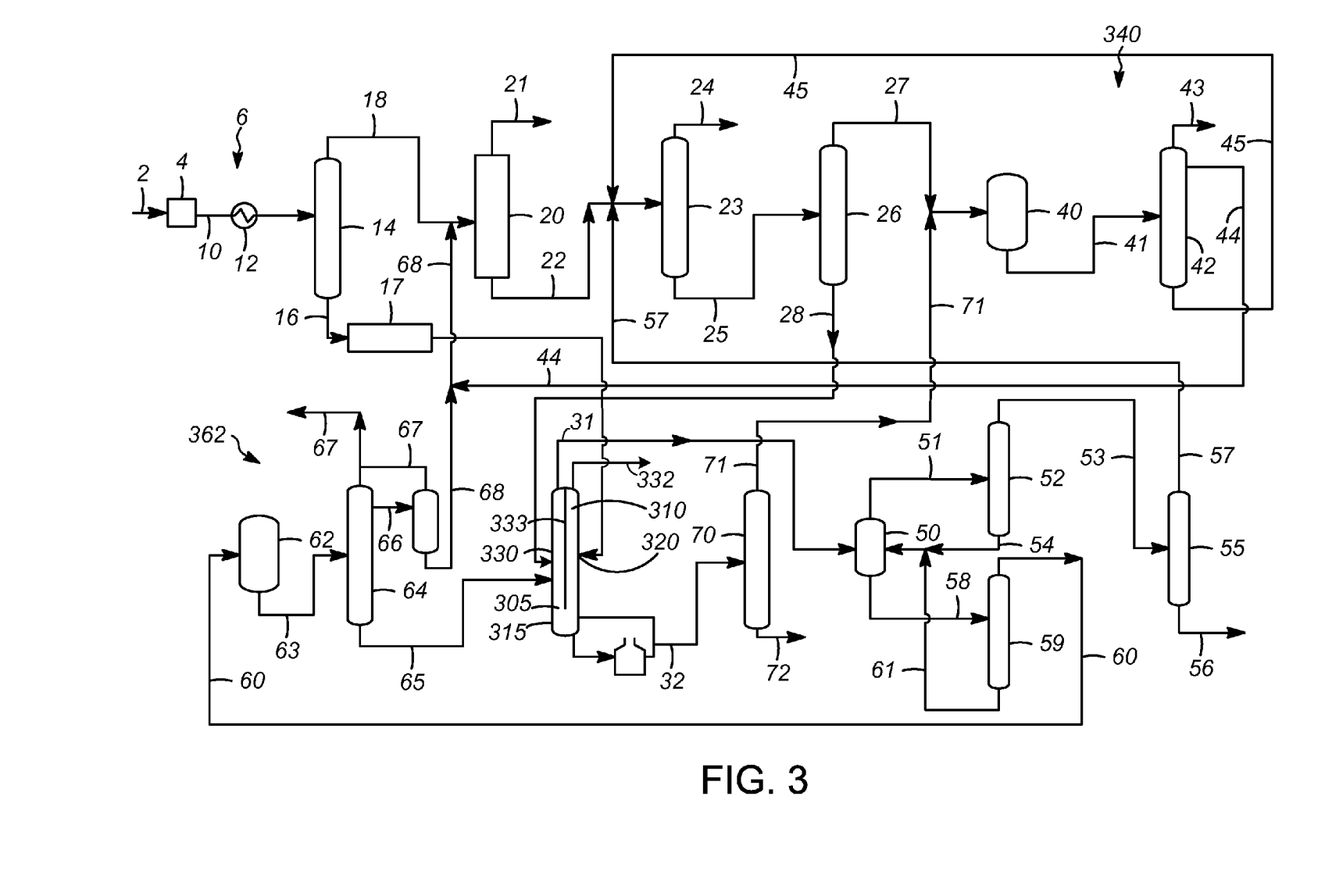
FIG. 3 illustrates an aromatics complex in accordance with various embodiments.

Turning now to FIG. 3, an aromatics complex and process in accordance with one aspect will be illustrated and described. As shown in FIG. 3, according to this aspect, the xylene fractionation column includes a split shell fractionation column 330. It includes a baffle 333 extending from the top of the column dividing the tray section of the fractionation column into two sides. The baffle extends to a height less than the full height of the split shell fractionation column so that a common bottom stream may be collected from below the baffle. A first stream enters the split shell fractionation column 330 on a first side 305 of the baffle 333. A second stream enters the column 330 on a second side 310 of the baffle 333. By one approach, the second stream has a higher mole ratio of ethylbenzene to total $C_8$ aromatic compounds than the first stream and therefore a higher ethylbenzene to total $C_8$ aromatics ratio. By one approach, the first stream has a ratio of ethylbenzene to total $C_8$ aromatics of between about 0.1 and about 10.0, between about 1.5 and about 2.5 in another example, and between about 3.0 and 5.0 in another example. On the other hand, by one example, the second stream has a ratio of ethylbenzene to total $C_8$ aromatics of between about 10.0 and about 25.0, between about 16.0 and about 18.0 in another example, and between about 12.0 and 14.0 in another example.

In the example illustrated in FIG. 3, the first stream includes a portion of a transalkylation zone effluent. The transalkylation zone effluent may be treated and or separated such as by fractionation prior to entering the split shell fractionation column 330. In one approach, the first stream includes at least a portion of a bottoms stream from the toluene column 26, which is passed to the inlet at the first side 305 of the split shell fractionation column via line 28. The second stream may include a reformate bottoms portion, such as the bottoms stream from reformate splitter 14 passed via line 16. The reformate bottoms stream may be treated, such as by clay treater 17 before entering the second side 310 of the split shell fractionation column 330. It has been identified that the toluene column bottoms stream has a lower ratio of ethylbenzene to total $C_8$ aromatics ratio than the reformate bottoms stream. The baffle 333 extends below the level of both feed inlets 315 and 320 and a normal operation liquid level of the split shell fractionation column 330 to allow the bottoms to mix.

The overhead stream extending from the transalkylation side 305 of the split shell fractionation column 330 including concentrated $C_8$ aromatics as overhead in conduit 31 from a high-boiling stream comprising $C_9$, $C_{10}$ and heavier aromatics as a bottoms stream in conduit 32. The $C_8$-aromatics overhead stream extending from the transalkylation side 305 of the split shell fractionation column 330 contains para-xylene, meta-xylene, ortho-xylene and ethylbenzene and passes via conduit 31 to para-xylene separation process 50.

The separation process operates, preferably via adsorption employing a desorbent, to provide a mixture of para-xylene and desorbent via conduit 51 to extract column 52, which separates para-xylene via conduit 53 from returned desorbent in conduit 54; the para-xylene is purified in finishing column 55, yielding a para-xylene product via conduit 56 and light material which is returned to benzene column 23 via conduit 57. A non-equilibrium mixture of $C_8$-aromatics raffinate and desorbent from separation process 50 is sent via conduit 58 to raffinate column 59, which separates a raffinate for isomerization in conduit 60 from returned desorbent in conduit 61.

The overhead stream extending from the reformate side 310 of the split shell fractionation column 330 including a mixed xylene product as overhead in conduit 332. By keeping the reformate side 310 and the transalkylation side 305 of the split shell fractionation column 330 separate, the xylene content of the paraxylene separation and xylene isomerization units are increased, thus increasing the quantity of the paraxylene that can be produced. A mixed xylene product is taken from the side containing a higher ratio of ethylbenzene to total $C_8$ aromatics.

The common bottoms from the split shell fractionation column 330 comprising $C_9+$ aromatics is sent via conduit 32 to heavies column 70, as described above with regard to FIG. 1. Since the baffle 333 extends from the bottom of the split shell fractionation column 330 to a height below the normal operation liquid level of the column, the liquid bottoms from the first (transalkylation effluent) side 305 and the second (reformate) side 310 segregates the high ethylbenzene content reformate mixed xylenes from the low ethylbenzene content streams. As illustrated in FIG. 3, the bottoms stream may be passed to the heavy aromatic hydrocarbon fractionation column 70 through conduit 32. In this regard, $C_9$ and $C_{10}$ aromatic compounds may be removed as an overhead stream from the fractionation column 70 and passed to the transalkylation reactor 40. Heavier compounds, including $C_{11+}$ aromatic compounds may be withdrawn as a bottoms stream via conduit 72. The heavy aromatic fractionation column bottoms stream may be sent to another location, such as, for example, blending with a gasoline pool where the aromatics complex is integrated with a refinery. Another portion of the bottoms stream may be recycled back to the second side 310 of the split shell fractionation column 330 after being passed through a reboiler.

Figure 4:
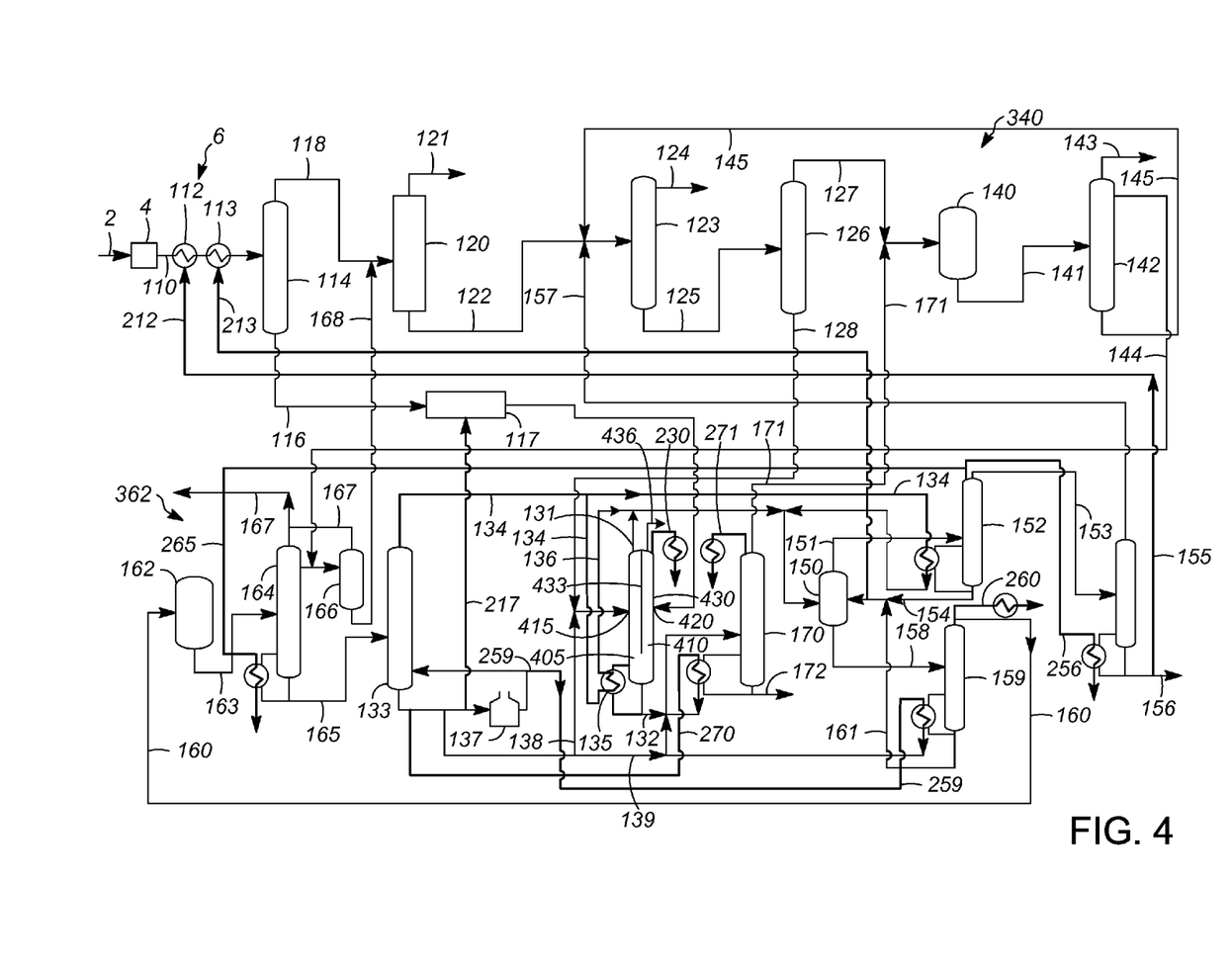
FIG. 4 illustrates an energy-efficient aromatics complex in accordance with various embodiments.

Turning now to FIG. 4, an energy-efficient aromatics complex and process incorporating a split shell fractionation column in accordance with an aspect is illustrated. As shown in FIG. 4, according to this aspect, the first xylene fractionation column includes a split shell fractionation column 430. The split shell fractionation column includes a baffle 433 extending from the top of the column dividing the tray section of the fractionation column 430 into two sides. The baffle extends to a height less than the full height of the split shell fractionation column so that a common bottom stream may be collected from below the baffle. A first stream enters the split shell fractionation column 430 on a first side 405 of the baffle 433. A second stream enters the column 430 on a second side 410 of the baffle 433. By one approach, the second stream has a higher ratio of ethylbenzene to total $C_8$ aromatic compounds than the first stream and therefore a higher ethylbenzene to total $C_8$ aromatics ratio. By one approach, the first stream has a ratio of ethylbenzene to total $C_8$ aromatics of between about 0.1 and about 10.0, between about 1.5 and about 2.5 in another example, and between about 3.0 and 5.0 in another example. On the other hand, by one example, the second stream has a ratio of ethylbenzene to total C$_8$ aromatics of between about 10.0 and about 25.0, between about 16.0 and about 18.0 in another example, and between about 12.0 and 14.0 in another example.

In the example illustrated in FIG. 4, the first stream includes a portion of a transalkylation zone effluent. The transalkylation zone effluent may be treated and or separated such as by fractionation prior to entering the split shell fractionation column 430. In one approach, the first stream includes at least a portion of a bottoms stream from the toluene column 126, which is passed to the inlet 415 at the first side 405 of the split shell fractionation column 430 via line 128. The second stream may include a reformate bottoms portion, such as the bottoms stream from reformate splitter 114 passed via line 116. The reformate bottoms stream may be treated, such as by clay treater 117 before entering the second side 410 of the split shell fractionation column 430. It has been identified that the toluene column bottoms stream has a lower ratio of ethylbenzene to total C$_8$ aromatic compounds than the reformate splitter bottoms stream. The baffle 433 extends below the level of both feed inlets 415 and 420 and a normal operation liquid level of the split shell fractionation column 430 to allow the bottoms to mix.

The overhead stream extending from the reformate side 410 of the split shell fractionation column 430 including a mixed xylene product as overhead in conduit 436. By keeping the reformate side 410 and the transalkylation side 405 of the split shell fractionation column 430 separate, the xylene content of the paraxylene separation and xylene isomerization units are increased, thus increasing the quantity of the paraxylene that can be produced. The overhead stream from the transalkylation side 405 from the split shell fractionation column 430 which may include some mixed xylenes is sent via conduit 131 to the para-xylene isomer separation unit 150 to separate para-xylene from the other xylene isomers and ethylbenzene as described above with regard to FIG. 2.

The common bottoms from the split shell fractionation column 430 comprising C$_9$+ aromatics is sent via conduit 132 to heavies column 170, as described above with regard to FIG. 2. Since the baffle 433 extends from the bottom of the split shell fractionation column 430 to a height below the normal operation liquid level of the column, the liquid bottoms from the first (transalkylation effluent) side 405 and the second (reformate) side 410 segregates the high ethylbenzene content reformate mixed xylenes from the low ethylbenzene content streams. The mixed xylene product may be taken from the side comprising the reformate stream.

The bottoms from the split shell fractionation column 430 are withdrawn as a bottoms stream through outlet 439 and at least a portion thereof is passed to the transalkylation reactor 140 via inlet 441. The transalkylation side bottoms stream may be further processed or separated prior to being passed to the transalkylation zone 440. For example, as illustrated in FIG. 4, the transalkylation side bottoms stream may be passed to the heavy aromatic hydrocarbon fractionation column 170 through inlet 471. In this regard, C$_9$ and C$_{10}$ aromatic compounds are removed as an overhead stream from the fractionation column 170 via outlet 472 and passed to the transalkylation reactor 140. Heavier compounds, including C$_{11+}$ aromatic compounds may be withdrawn as a bottoms stream via conduit 172. The heavy aromatic fractionation column bottoms stream may be sent to another location, such as, for example, blending with a gasoline pool when the aromatics complex is integrated in a refinery. Another portion of the first xylene column bottoms stream may be passed via conduit 435 to reboiler 135 and back to the first side 405 of the split shell fractionation column 430. While not illustrated, a portion of the reformate side bottoms stream may be separated and passed to a reboiler and back to the reformate side 410 of the split shell fractionation column 430.

While the present disclosure herein disclosed has been described by means of specific embodiments, examples and applications thereof, numerous modifications and variations could be made thereto by those skilled in the art without departing from the scope of the present disclosure set forth in the claims.

SPECIFIC EMBODIMENTS

While the following is described in conjunction with specific embodiments, it will be understood that this description is intended to illustrate and not limit the scope of the preceding description and the appended claims.

A first embodiment of the invention is an apparatus for producing one or more xylenes, comprising a split shell fractionation column having an outer reactor shell and a baffle extending downward from an upper portion of the split shell fractionation column to a height less than a height of the fractionation column and separating the column into a first side and a second side; an inlet to the first side of the fractionation column in fluid communication with an outlet of a transalkylation zone; an inlet to the second side of the fractionation column in fluid communication with an outlet of a reforming zone; a first overhead outlet in communication with the first side of the fractionation column for withdrawing a C$_8$ aromatics enriched stream; a second overhead outlet in communication with the second side of the fractionation column for withdrawing a C$_8$ aromatics enriched stream; and a bottoms outlet of the fractionation column for withdrawing a bottoms stream. An embodiment of the invention is one, any or all of prior embodiments in this paragraph up through the first embodiment in this paragraph, further comprising a reforming zone comprising a reforming catalyst for reforming one or more hydrocarbon compounds to increase aromatic compounds. An embodiment of the invention is one, any or all of prior embodiments in this paragraph up through the first embodiment in this paragraph, further comprising a transalkylation zone comprising a transalkylation catalyst for transalkylating C$_7$ and C$_9$ aromatic compounds. An embodiment of the invention is one, any or all of prior embodiments in this paragraph up through the first embodiment in this paragraph, wherein the bottoms outlet is in communication with an inlet of the transalkylation zone. An embodiment of the invention is one, any or all of prior embodiments in this paragraph up through the first embodiment in this paragraph, wherein the first overhead outlet is in fluid communication with a para-xylene recovery zone. An embodiment of the invention is one, any or all of prior embodiments in this paragraph up through the first embodiment in this paragraph, wherein the second overhead outlet is in fluid communication with a mixed xylene product pool. An embodiment of the invention is one, any or all of prior embodiments in this paragraph up through the first embodiment in this paragraph, further comprising an isomerization zone including an isomerization reactor and an isomerization catalyst; and an outlet of the isomerization zone in fluid communication with at least one of the inlet to the first side, the inlet to the second side, or another inlet of the split shell fractionation column. An embodiment of the invention is one, any or all of prior embodiments in this paragraph up through the first embodiment in this paragraph, further comprising a second xylene fractionation column between the isomerization zone and the split shell fractionation column, the second xylene fractionation column comprising an inlet in fluid communication with the isomerization zone outlet; an overhead outlet for removing an overhead stream including xylenes; and a bottoms outlet in communication with the at least one of the inlet to the first side, the inlet to the second side, or the other inlet of the split shell fractionation column for passing a bottoms stream from the second xylene column to the split shell fractionation column.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. An apparatus for producing one or more xylenes, comprising:
    a split shell fractionation column having an outer reactor shell and a baffle extending downward from an upper portion of the split shell fractionation column to a height less than a height of the fractionation column and separating the column into a first side and a second side;
    an inlet to the first side of the fractionation column in fluid communication with
    an outlet of a transalkylation zone;
    an inlet to the second side of the fractionation column in fluid communication with an outlet of a reforming zone;
    a first overhead outlet in communication with the first side of the fractionation column for withdrawing a C8 aromatics enriched stream;
    a second overhead outlet in communication with the second side of the fractionation column for withdrawing a C8 aromatics enriched stream;
    a bottoms outlet of the fractionation column for withdrawing a bottoms stream; and
    further comprising a reforming zone comprising a reforming catalyst for reforming one or more hydrocarbon compounds to increase aromatic compounds.

2. The apparatus according to claim 1, further comprising a transalkylation zone comprising a transalkylation catalyst for transalkylating C7 and C9 aromatic compounds.

3. The apparatus according to claim 1, wherein the first overhead outlet is in fluid communication with a para-xylene recovery zone.

4. The apparatus according to claim 3, further comprising a second xylene fractionation column between the isomerization zone and the split shell fractionation column, the second xylene fractionation column comprising:
    an inlet in fluid communication with the isomerization zone outlet;
    an overhead outlet for removing an overhead stream including xylenes; and
    a bottoms outlet in communication with the at least one of the inlet to the first side, the inlet to the second side, or the other inlet of the split shell fractionation column for passing a bottoms stream from the second xylene column to the split shell fractionation column.

5. The apparatus according to claim 1, wherein the second overhead outlet is in fluid communication with a mixed xylene product pool.

6. The apparatus according to claim 1, further comprising an isomerization zone including an isomerization reactor and an isomerization catalyst; and
    an outlet of the isomerization zone in fluid communication with at least one of the inlet to the first side, the inlet to the second side, or another inlet of the split shell fractionation column.

* * * * *